United States Patent
Hagmann et al.

(10) Patent No.: US 6,482,840 B2
(45) Date of Patent: Nov. 19, 2002

(54) SUBSTITUTED CYCLIC AMIDINE DERIVATIVES AS INHIBITORS OF CELL ADHESION

(75) Inventors: William K. Hagmann, Westfield, NJ (US); George A. Doherty, Princeton, NJ (US); Shrenik Shah, Metuchen, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/862,194

(22) Filed: May 21, 2001

(65) Prior Publication Data

US 2002/0010199 A1 Jan. 24, 2002

Related U.S. Application Data

(60) Provisional application No. 60/206,183, filed on May 22, 2000.

(51) Int. Cl.$^7$ .................. A61K 31/44; C07D 213/02
(52) U.S. Cl. .................. 514/352; 546/312
(58) Field of Search .................. 546/312; 514/352

(56) References Cited

FOREIGN PATENT DOCUMENTS

GB        2255557     * 11/1992
JP        08291143    * 11/1996

* cited by examiner

*Primary Examiner*—Zinna Northington Davis
(74) *Attorney, Agent, or Firm*—Mollie M. Yang; David L. Rose

(57) ABSTRACT

Compounds of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of AIDS-related dementia, allergic conjunctivitis, allergic rhinitis, Alzheimer's disease, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, multiple myeloma, myocarditis, organ transplantation, psoriasis, pulmonary fibrosis, restenosis, retinitis, rheumatoid arthritis, septic arthritis, stroke, tumor metastasis, uveititis, and type I diabetes.

4 Claims, No Drawings

US 6,482,840 B2

SUBSTITUTED CYCLIC AMIDINE DERIVATIVES AS INHIBITORS OF CELL ADHESION

CROSS REFERENCE TO RELATED APPLICATIONS

This application claims priority from provisional application No. 60/206,183 filed on May 22, 2000, which is hereby incorporated by reference in its entirety.

SUMMARY OF THE INVENTION

The compounds of the present invention are antagonists of the VLA-4 integrin ("very late antigen-4"; CD49d/CD29; or $\alpha_4\beta_1$) and/or the $\alpha4\beta7$ integrin (LPAM-1 and $\alpha_4\beta_p$), thereby blocking the binding of VLA-4 to its various ligands, such as VCAM-1 and regions of fibronectin, and $\alpha4\beta7$ to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4- and/or $\alpha4\beta7$-binding and cell adhesion and activation, such as AIDS-related dementia, allergic conjunctivitis, allergic rhinitis, Alzheimer's disease, aortic stenosis, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, myocarditis, organ transplantation, psoriasis, restenosis, retinitis, rheumatoid arthritis, septic arthritis, stroke, tumor metastasis, type I diabetes, and vascular occlusion following angioplasty.

BACKGROUND OF THE INVENTION

The present invention relates to susbstituted cyclic amine derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, N.Y., 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of these cell types (see M. E. Hemler, "VLA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to proinflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, N.Y., 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." *J. Rheumatol.*, 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", *J. Clin. Invest.*, 93, 1700 (1994), A. Jakubowski et al., "Vascular cell adhesion molecule-Ig fusion protein selectively targets activated α4-integrin receptors in vivo: Inhibition of autoimmune diabetes in an adoptive transfer model in nonobese diabetic mice." *J. Immunol.*, 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Tranplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts." *J. Clin Invest.*, 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin α-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of α4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996); xii) inhibition of TH2 T-cell cytokine production including IL-4 and IL-5 by VLA-4 antibodies which would attenuate allergic responses (J.Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas, including multiple myeloma; inflammatory lung disorders; acute respiratory distress syndrome (ARDS); pulmonary fibrosis; atherosclerotic plaque formation; restenosis; uveitis; and circulatory shock (for examples, see A. A. Postigo et al., "The $\alpha_4\beta_1$/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren®, Athena Neurosciences/Elan ) against VLA-4 in clinical development for the treatment of multiple sclerosis and Crohn's disease and a humanized monoclonal antibody (ACT-1/®/LDP-02 Millenium/Genentech) against $\alpha_4\beta_7$ in clinical development for the treatment of inflammatory bowel disease. Several classes of antagonists of VLA-4 and α4β7 have been described: (D. Y. Jackson et al., "Potent α4β1 peptide antagonists as potential anti-inflammatory agents", *J. Med. Chem.*, 40, 3359 (1997); H. N. Shroff et al., "Small peptide inhibitors of α4β7 mediated MadCAM-1 adhesion to lymphocytes", *Bioorg. Med. Chem. Lett.*, 6, 2495 (1996); A. J. Soures et al., *Bioorg. Med. Chem. Lett.*, 8, 2297 (1998); K. C. Lin et al., "Selective, tight-binding inhibitors of integrin α4β1 that inhibit allergic airway responses", *J. Med. Chem.*, 42, 920 (1999); S. P. Adams and R. R. Lobb, "Inhibitors of Integrin Alpha 4 Beta 1 (VLA-4)." in Ann. Repts. in Medicinal Chemistry, Vol. 34, A. M. Doherty, Ed.; Acad. Press, N.Y., 1999, p. 179; L. Chen et al.,"N-Acyl phenyhlalanine analogues as VCAM/VLA-4 antagonists", *Bioorg. Med. Chem. Lett.*, 10, 725 (2000); L. Chen et al.,"N-Benzylpyroglutamate-L-phenyhlalanine derivatives as potent small molecule VLA-4 antagonists", *Bioorg. Med. Chem. Lett.*, 10, 729 (2000);U.S. Pat. No. 5,510,332, WO00/18759, WO00/18760, WO00/15612, WO00/05224, WO00/05223, WO00/01690, WO00/00477, WO99/67230, WO99/61465, WO99/54321, WO99/47547, WO99/43642, WO99/37618, WO99/37605, WO99/36393, WO99/35163, WO99/24398, WO99/23063, WO98/58902, WO98/54207, WO97/03094, WO97/02289, WO96/40781, WO96/40641, WO96/31206, WO96/22966, WO96/20216, WO96/06108, WO96/01644, WO95/15973, EP0918059A1, EP0842943A2, EP0905139A2, EP0903353A1,. There still remains a need for low molecular weight, specific inhibitors of VLA-4 and α4β7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and α4β7 binding and cell adhesion and activation.

DETAILED DESCRIPTION OF THE INVENTION

The present invention provides novel compounds of formula I:

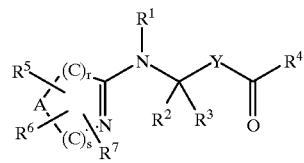

or a pharmaceutically acceptable salt thereof wherein:
$R^1$ is
1) hydrogen,
2) $C_{1-10}$alkyl,
3) $C_{2-10}$alkenyl,
4) $C_{2-10}$alkynyl,
wherein alkyl, alkenyl and alkynyl are optionally substituted with one to four substituents independently selected from $R^a$;

$R^2$ is
1) $C_{1-10}$alkyl,
2) $Ar^1$,
3) $Ar^1$—$C_{1-10}$alkyl,
4) $Ar^1$—$Ar^2$,
5) $Ar^1$—$Ar^2$—$C_{1-10}$alkyl-,
wherein the alkyl group is optionally substituted with one to four substituents selected from $R^a$, and $Ar^1$ and $Ar^2$ are optionally substituted with one to four substituents independently selected from $R^b$, $R^3$ is
1) hydrogen,
2) $C_{1-10}$alkyl,
3) $C_{2-10}$alkenyl,
4) $C_{2-10}$alkynyl,
wherein alkyl, alkenyl and alkynyl are optionally substituted with one to four substituents independently selected from $R^a$;

$R^4$ is
1) hydroxy,
2) $C_{1-10}$alkoxy,
3) $C_{2-10}$alkenyloxy,
4) $C_{2-10}$alkynyloxy,
5) Cy-O—,
6) Cy-$C_{1-10}$alkoxy,
7) amino,
8) $C_{1-10}$alkylamino,
9) di($C_{1-10}$alkyl)amino,
10) Cy-$C_{1-10}$alkylamino,
wherein alkyl, alkenyl and alkynyl are optionally substituted with one to four substituents selected from $R^a$, and Cy is optionally substituted with one to four substituents independently selected from $R^b$;

$R^5$, $R^6$, and $R^7$ are independently selected from
1) hydrogen,
2) $C_{1-10}$ alkyl,
3) $C_{2-10}$ alkenyl,
4) $C_{2-10}$ alkynyl,
5) cycloalkyl,
6) heterocyclyl,
7) aryl;
8) aryl $C_{1-10}$alkyl,
9) heteroaryl;
10) heteroaryl $C_{1-10}$alkyl,
11) —$OR^d$,
13) —$NO_2$,
14) halogen
15) —$S(O)_m R^d$,
16) —$SR^d$,
17) —$S(O)_2 OR^d$,
8) —$S(O)_m NR^d R^e$,
19) —$NR^d R^e$,
20) —$O(CR^f R^g)_n NR^d R^e$,
21) —$C(O)R^d$,
22) —$CO_2 R^d$,
23) —$CO_2(CR^f R^g)_n CONR^d R^e$,
24) —$OC(O)R^d$,
25) —CN,
26) —$C(O)NR^d R^e$,
27) —$NR^d C(O)R^e$,
28) —$OC(O)NR^d R^e$,
29) —$NR^d C(O)OR^e$,
30) —$NR^d C(O)NR^d R^e$,
31) —$CR^d(N\text{—}OR^e)$,
32) $CF_3$; or
33) —$OCF_3$;
wherein alkyl, alkenyl, alkynyl, cycloalkyl, heterocyclyl, aryl, heteroaryl are optionally substituted with one to four substituents selected from a group independently selected from $R^b$, with the proviso that when $R^5$, $R^6$, or $R^7$ are attached to the ring by nitrogen, sulfur or oxygen, they may not be atached to the ring atom adjacent to A when A is other than carbon; or $R^5$ and $R^6$ together with the atom or atoms to which they are attached form a fused or spirocyclic ring of 4 to 7 members containing 0–2 heteroatoms independently selected from oxygen, sulfur and nitrogen;

$R^8$ is
1) hydrogen,
2) $C_{1-10}$ alkyl,
3) $C_{2-10}$ alkenyl,
4) $C_{2-10}$ alkynyl,
5) aryl,
6) heteroaryl,
7) aryl $C_{1-10}$alkyl,
8) heteroaryl $C_{1-10}$ alkyl,
9) —$OR^d$,
10) —$O(CR^f R^g)_n NR^d R^e$,
11) —$OC(O)R^d$,
12) —$OC(O)NR^d R^e$,
13) halogen,
14) —$SR^d$,
15) —$S(O)_m R^d$,
16) —$S(O)_2 OR^d$,
17) —$S(O)_m NR^d R^e$,
18) —$NO_2$,
19) —$NR^d R^e$,
20) —$NR^d C(O)R^e$,
21) —$NR^d S(O)_m R^e$,
22) —$NR^d C(O)OR^e$, or
23) —$NR^d C(O)NR^d R^e$,
wherein alkyl, alkenyl, alkynyl, aryl, heteroaryl are optionally substituted with one to four substituents selected from a group independently selected from $R^c$;

$R^9$ is
1) hydrogen,
2) $C_{1-10}$ alkyl,
3) $C_{2-10}$ alkenyl,
4) $C_{2-10}$ alkynyl,
5) cycloalkyl,
6) heterocyclyl,
7) aryl,
8) heteroaryl;
9) aryl $C_{1-10}$alkyl,
10) heteroaryl $C_{1-10}$ alkyl,
wherein alkyl, alkenyl, alkynyl, cycloalkyl, heterocyclyl, aryl, heteroaryl are optionally substituted with one to four substituents selected from a group independently selected from $R^c$;

$R^a$ is
1) hydrogen,
2) —$OR^d$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N—OR^e)$,
22) $CF_3$; or
23) —$OCF_3$;
$R^b$ is
1) a group selected from $R^a$,
2) $C_{1-10}$ alkyl,
3) $C_{2-10}$ alkenyl,
4) $C_{2-10}$ alkynyl,
5) cycloalkyl,
6) heterocyclyl,
7) aryl;
8) aryl $C_{1-10}$alkyl,
9) heteroaryl;
10) heteroaryl $C_{1-10}$ alkyl,
wherein alkyl, alkenyl, alkynyl, cycloalkyl, heterocyclyl, aryl, heteroaryl are optionally substituted with one to four substituents selected from a group independently selected from $R^c$;
$R^c$ is
1) halogen,
2) —$NR^dR^e$,
3) carboxy,
4) cyano,
5) $C_{1-4}$alkyl,
6) $C_{1-4}$alkoxy,
7) aryl,
8) aryl $C_{1-4}$alkyl,
9) heteroaryl,
10) hydroxy,
11) —$CF_3$,
wherein alkyl, alkenyl, alkynyl, cycloalkyl, heterocyclyl, aryl, heteroaryl are optionally substituted with one to four substituents selected from a group independently selected from $R^c$;
$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atoms to which they are attached form a heterocyclic ring of 4 to 7 members containing 0–2 additional heteroatoms independently selected from oxygen, sulfur and nitrogen;
$R^f$ and $R^g$ are independently selected from hydrogen, $C_{1-10}$alkyl, Cy and Cy-$C_{1-10}$alkyl; or
$R^f$ and $R^g$ together with the carbon to which they are attached form a ring of 4 to 7 members containing 0–2 heteroatoms independently selected from oxygen, sulfur and nitrogen;
$R^h$ is
1) hydrogen,
2) —$OR^d$,
3) —$NO_2$,
4) —$S(O)_mR^d$,
5) —$S(O)_2OR^d$,
6) —$NR^dR^e$,
7) —$C(O)R^d$,
8) —$CO_2R^d$,
9) —CN,
10) —$C(O)NR^dR^e$,
11) $C_{1-10}$ alkyl,
12) $C_{2-10}$ alkenyl,
13) $C_{2-10}$ alkynyl,
14) cycloalkyl,
15) heterocyclyl,
16) aryl;
17) aryl $C_{1-10}$alkyl,
18) heteroaryl, or
19) heteroaryl $C_{1-10}$ alkyl,
wherein alkyl, alkenyl, alkynyl, cycloalkyl, heterocyclyl, aryl, heteroaryl are optionally substituted with one to four substituents selected from a group independently selected from $R^c$;
Cy is independently selected from cycloalkyl, heterocyclyl, aryl, or heteroaryl;
$Ar^1$ and $Ar^2$ are independently selected from aryl and heteroaryl;
m is an integer from 1 to 2;
n is an integer from 1 to 10;
r is an integer from 0 to 4;
s is an integer from 1 to 5;
r+s is an integer from 2 to 5 when A is carbon, oxygen, N—(Rh)— or —S(O)m-;
r+s is an integer from 1 to 4 when A is —C(=O)N($R^h$)—, —O—N($R^h$)— or S(O)$_2$N($R^h$)—;
A is
1) carbon,
2) oxygen,
3) —N($R^h$)—,
4) —C(=O)N($R^h$)—,
5) —O—N($R^h$)—,
6) —S(O)$_2$N($R^h$)—,
7) —$S(O)_m$;
Y is
1) a bond, or
2) —C($R^8$)($R^9$)-.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon—carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Examples of the heterocycle

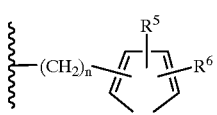

include, but are not limited to,

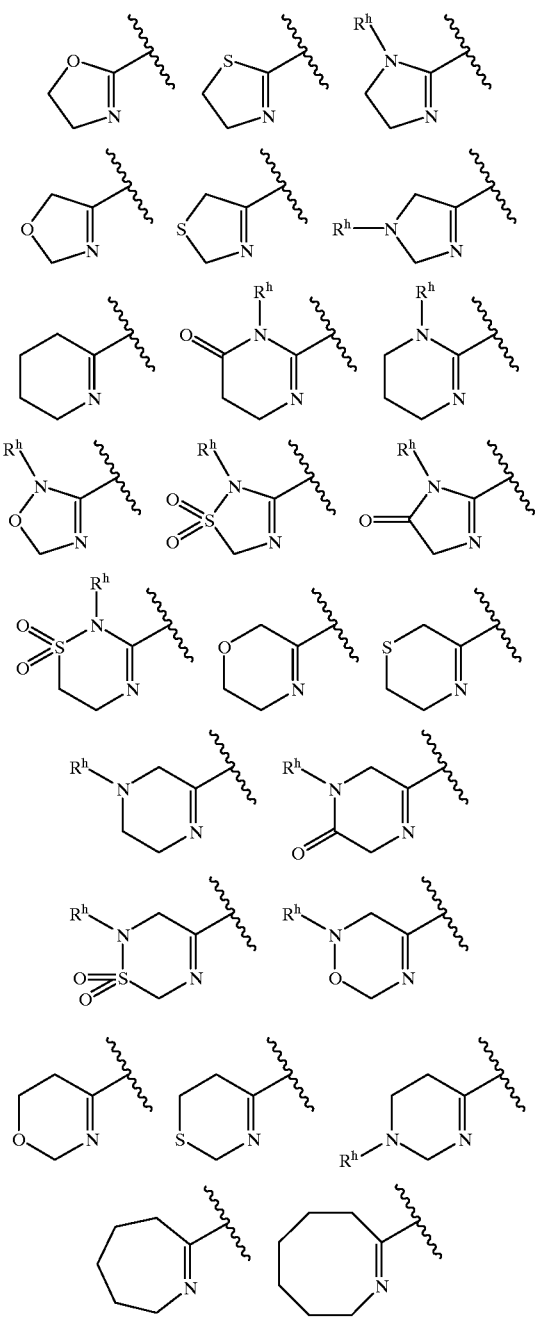

In another subset of compounds of formula I, Y is a bond, R3 is hydrogen, and R2 is Ar1—Ar2, Ar1—Ar2—C1-10alkyl, Ar1 or Ar1—C1–10alkyl wherein Ar1 and Ar2 are optionally substituted with one to four groups selected from Rb. Examples of suitable R2 within this subset are:

(1)

wherein W, n, R5 and R6 are as defined in PCT Published Application WO 99/36393 (Tanabe); the relevant definitions as well as specific exemplification of such definitions are hereby incorporated by reference;

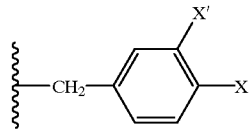
(2)

wherein X and X' are as defined in WO99/10312 (Hoffmann-LaRoche); the relevant definitions as well as specific exemplification of such definitions are hereby incorporated by reference;

(3) —(CH2)x—Ar-R5' wherein x, Ar, R5' are as defined in Athena's WO99/06431, WO99/06434, WO99/06390; the relevant definitions as well as specific exemplification of such definitions are hereby incorporated by reference.

(4) —(CH2)—X wherein X, to the extent it is within the scope of Ar1 and Ar1—Ar2, is as defined in Athena's WO99/06437, WO99/06433, WO99/06435;

(5) —(CH2)n-aryl or —(CH2)n-heteroaryl, wherein n and aryl and heteroaryl are as defined in WO99/06436 (Athena);

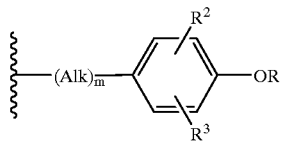
(6)

wherein Alk, m, R, R2, R3 are as defined in WO98/54207 (Celltech).

(7) Ar1—Ar2—C1–10alkyl wherein Ar1 and Ar2 are as defined in WO98/53817;

(8) Cy or Cy-C1–10alkyl, wherein Cy to the extent it is within the scope of Ar1, is as defined in WO98/53818.

In another subset of compounds of formula I, R7 is CO2H and pharmaceutically acceptable salt thereof.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or α4β7 integrin makes them useful for preventing or reversing the symptoms, disorders or diseases induced by the binding of VLA-4 and or α4β7to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or α4β7 binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, and (19) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (1) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying Schemes. Appropriately protected amino acid derivatives may be synthesized as outlined in Scheme 1. N-(t-Butyloxycarbonyl) amino acid A is treated with t-butyl 2,2,2-trichloroacetimidate in the presence of a Lewis acid (boron trifluoride-etherate) to form protected amino acid ester B. Likewise, the free amino acid C is reacted with isobutylene in the presence of sulfuric acid to form t-butyl ester followed by reaction with BOC-ON to form B.

Scheme 1

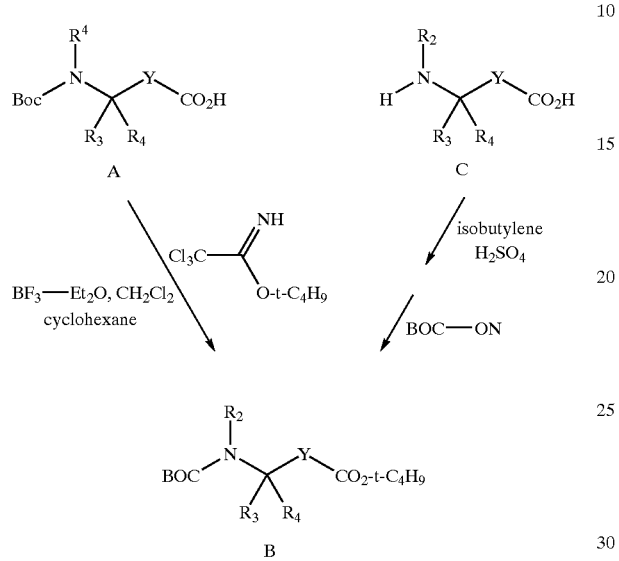

Biaryl amino acid derivatives are prepared by application of Stille-type carbon—carbon bond forming conditions (A. M. Echavarren and J. K. Stille, *J. Am. Chem. Soc.*, 109, 5478 (1987); Farina et al., *J. Org. Chem.* 5434, (1993)). In Scheme 2, the aryl bromide or iodide intermediate A is converted into its trialkyltin derivative B using hexamethylditin $(((CH_3)_3Sn)_2)$ in the presence of a palladium(0) catalyst and lithium chloride and then reacted with an appropriately substituted aryl or heteroaryl bromide, iodide, or triflate in the presence of a palladium reagent, such as tetrakis(triphenylphosphine)palladium(0) or tris(dibenzylideneacetone)dipalladium(0), in a suitable solvent, such as toluene, dioxane, DMF, or 1-methyl-2-pyrrolidinone, followed by the removal of the tert-butyl ester using strong acid (TFA) to yield the desired product C. The BOC protecting group is subsequently removed treatment with strong acid (HCl, $H_2SO_4$, or TFA) to form D.

Scheme 2

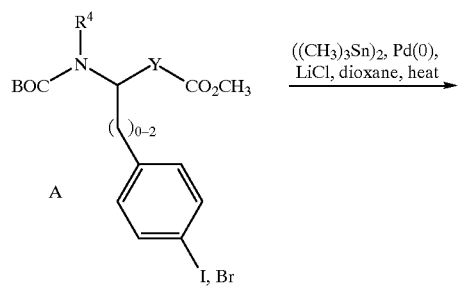

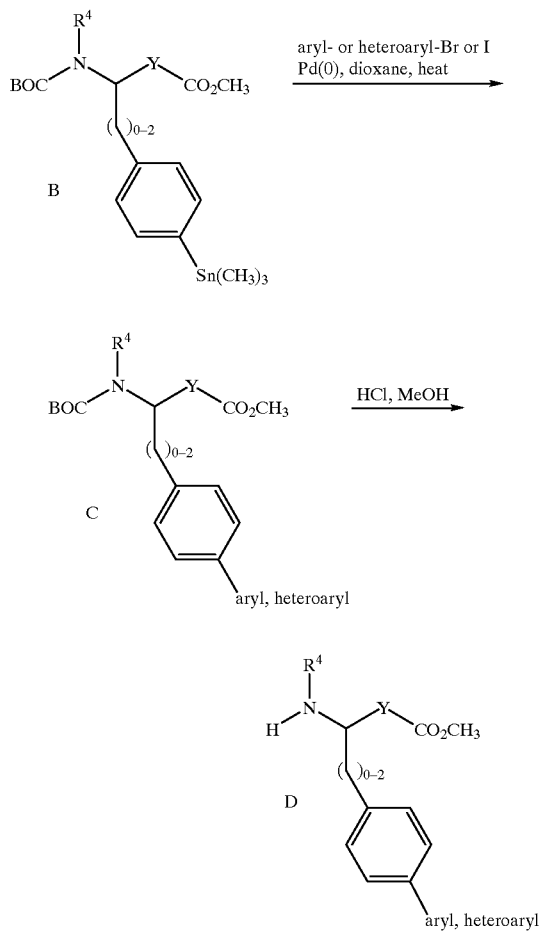

Alternatively, a boronate ester derivative A is carefully hydrolyzed to the boronic acid B (Scheme 3). Substituted aryl- or heteroaryl-halides or -triflates are coupled to B in the presence of a palladium(0) reagent, such as tetrakis(triphenylphosphine)palladium under Suzuki conditions (N. Miyaura et al., *Synth. Commun.*, 1981, 11, 513–519) to form C. Alternatively, alkene derivatives, acid chlorides or amides may be coupled to the boronic acid to form C. The BOC group may be selectively removed in the presence of sulfuric acid in t-butyl acetate to yield amino acid ester D.

Scheme 3

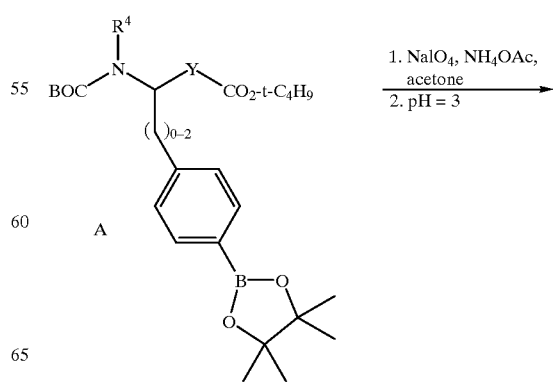

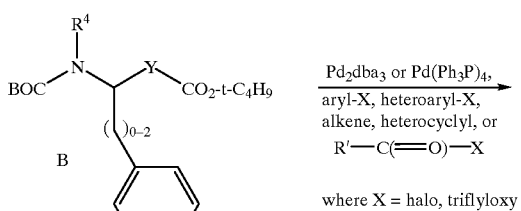

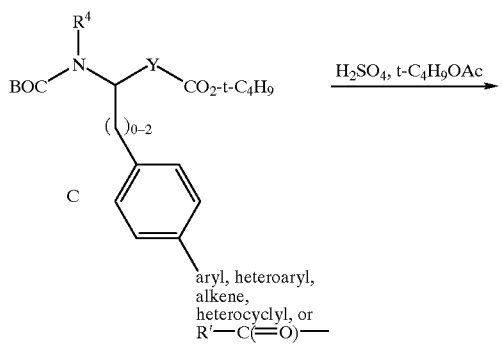

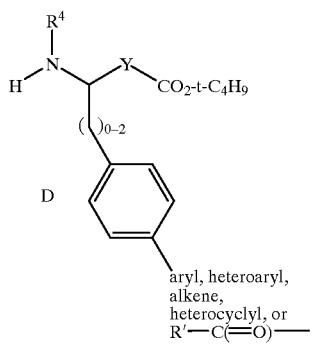

Lactams A are treated with Lawesson's reagent to form thiolactam B (Scheme 4). Alkylation with methyliodide or dimethylsulfate produces isothiouronium salt C. Amino acid ester D is reacted with C to form amidine derivative E. Treatment of ester E with strong acid (TFA or HCl) produces the desired amidine acid F.

Scheme 4

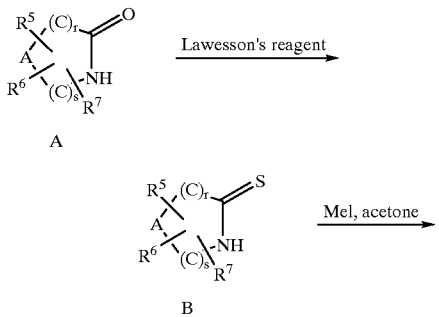

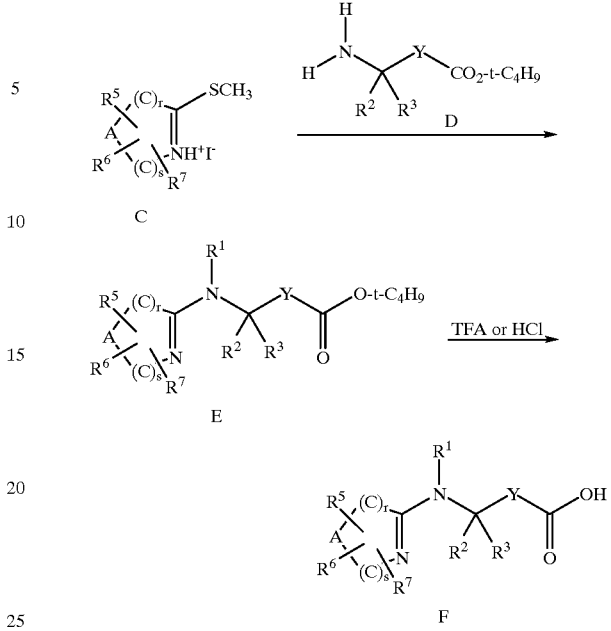

The starting materials used in the various schemes depicted above are either commercially available or may be prepared according to known methods in the art.

| Abbreviations | |
|---|---|
| Ac$_2$O: | acetic anhydride |
| BF$_3$—Et$_2$O: | borontrifluoride etherate |
| Bn: | benzyl |
| BOC: | tert-butyloxycarbonyl |
| BOC-ON: | 2-(tert-butoxycarbonyloxyimino)-2-phenylacetonitrile |
| BOP: | benzotriazol-1-yloxy-tris (dimethylamino)-phosphonium hexafluorophosphate |
| t-Bu$_3$P: | tri-tert-butylphosphine |
| CBZ: | benzyloxycarbonyl |
| CH$_2$Cl$_2$: | methylene chloride |
| CH$_3$CN: | acetonitrile |
| CH$_3$NO$_2$: | nitromethane |
| CsOH: | cesium hydroxide |
| Cy$_3$P: | tricyclohexylphosphine |
| DIBAL-H: | diisobutylaluminum hydride |
| DBU: | 1,8-diazobicyclo[5.4.0]undec-7-ene |
| DCC: | dicyclohexylcarbodiimide |
| DIEA: | N,N-diisopropylethylamine |
| DMF: | dimethylformamide |
| DMSO: | dimethylsulfoxide |
| EDC: | 1-(ethyl)-3-(3-dimethylaminopropyl)-carbodiimide hydrochloride |
| Et: | ethyl |
| EtOAC: | ethyl acetate |
| EtOH: | ethanol |
| FMOC: | 9-fluorenylmethoxylcarbonyl |
| H$_2$SO$_4$: | sulfuric acid |
| HATU: | O-(7-azabenzotriazol-1-yl)-1,1,3,3-tetramethyluronium hexafluorophosphate |
| HBTU: | O-(benzotriazole-1-yl)-1,1,3,3-tetramethyluronium hexafluorophosphate |
| HCl: | hydrochloric acid |
| HOAt: | 1-hydroxy-7-azabenzotriazole |
| HOBt: | 1-hydroxybenzotriazole |
| HPLC: | high pressure liquid chromatography |
| K$_2$CO$_3$: | potassium carbonate |
| KF: | potassium fluoride |
| KI: | potassium iodide |
| LDA: | lithium diisopropylamide |
| Me: | methyl |

-continued

Abbreviations

| | |
|---|---|
| MeOH: | methanol |
| MgSO$_4$: | madnesium sulfate |
| mmol: | millimole |
| MPLC: | medium pressure liquid chromatography |
| MsCl: | methanesulfonyl chloride |
| NaHCO$_3$: | sodium bicarbonate |
| NaOH: | sodium hydroxide |
| NBS: | N-bromosuccinimide |
| Pd$_2$dba$_3$: | tris(dibenzylideneacetone) dipalladium(0) |
| Ph: | phenyl |
| Ph$_3$P: | triphenylphosphine |
| PyBOP: | (benzotriazol-1-yloxy)tripyrrolidinophosphonium hexafluorophosphate |
| TBAF: | tetrabutylammonium fluoride |
| TBSCl: | tert-butyldimethylsilyl chloride |
| TFA: | trifluoroacetic acid |
| THF: | tetrahydrofuran |
| TLC: | thin layer chromatography |
| TMSCHN$_2$: | trimethylsiliyldiazomethane |

REFERENCE EXAMPLE 1

(L)-4-(2'-Cyanophenyl)phenylalanine, methyl ester hydrochloride

Step A (L)-4-Iodophenylalanine, methyl ester hydrochloride

Thionyl chloride (3.6 mL, 50 mmol) was slowly added dropwise to a stirred flask containing methanol (6 mL) at 0° C. Ater the addition, solid N-BOC-(L)-4-iodophenylalanine (3.9 gm, 10 mmol) was added followed by more methanol (10 mL). The was refluxed for 1.5 hr and then cooled to room temperature. The solution taken to dryness by rotoevaporation and ether (20 mL) and heptane (5 mL) were added. The suspension was again taken to dryness by rotoevaporation and used in the subsequent reaction.

Step B

N-BOC-(L)-4-Iodophenylalanine, methyl ester

The product from Step A (10 mmol) was suspended in TBF (20 mL) and methylene chloride (10 mL) at room temperature and triethylamine (2.1 mL, 11 mmol) was added. BOC-ON (2.7 gm, 11 mmo) was added and the solution stirred at room temperature for 5.5 hr. The solution was poured into a mixture of water (100 mL) and EtOAc (100 mL) and separated. The aqueous portion was extracted with EtOAc (2×50 mL). The combined organic extracts were washed successively with 5% citric acid (50 mL), saturated sodium bicarbonate solution (50 mL), and brine (50 mL) and dried over anhydrous magnesium sulfate. The mixture was filtered and concentrated to an oily residue which was dissolved in ether (50 mL) and placed in a freezer overnight. As no crystals precipitated, the solution was azeotroped with hexanes (2×50 mL) and the residue purified by flash column chromatography on silica gel eluted with 10% EtOAc in hexanes. Concentration of the chromatography fractions yielded N-BOC-(L)-4-iodophenylalanine, methyl ester (3.1 gm).

Step C

N-BOC-(L)-4-Trimethylstannyl-phenylalanine, methyl ester

To a degassed solution of N-BOC-(L)-4-iodophenylalanine, methyl ester (3.1 gm, 7.6 mmol), hexamethylditin (2.2 mL, 11.4 mmol), lithium chloride (0.5 gm, 11.4 mmol), and triphenylphosphine (40 mg, 0.2 mmol) in dioxane was added tetrakis(triphenylphosphine)palladium (II) (0.44 gm, 0.4 mmol). The solution was heated to 95° C. overnight under a dry nitrogen atmosphere. The solution was cooled to room temperature and diluted with EtOAc (100 mL) and successively washed with saturated sodium bicarbonate solution and saturated brine. The solution was dried over anhydrous magnesium sulfate, filtered, and concentrated with dry silica gel. The dry powder was placed on a silica gel column and the product purifed by flash column chromatography eluted with 10% EtOAc in hexanes to yield N-BOC-(L)-4-trimethylstannyl-phenylalanine, methyl ester (1.5 gm).

Step D

N-BOC-(L)-4-(2'-Cyanophenyl)phenylalanine, methyl ester

To a degassed solution of N-BOC-(L)-4-trimethylstannyl-phenylalanine, methyl ester (1.4 gm,3.2 mmol) and 2-bromobenzonitrile (1.2 gm, 6.3 mmol) in DMF (8 mL) was added bis(triphenylphosphine)palladium(II)chloride (224 mg, 0.32 mmol). The stirred mixture was placed into a preheated oil bath (90° C.) and stirred for 3.5 hr. Heating was stopped and the solution allowed to cool. The solvent was removed by rotoevaporation and the residue dissolved in methylene chloride. The product was purifed on silica gel using a Biotage flash column chromatography apparatus eluted with 15% EtOAc in hexanes to yield N-BOC-(L)-4-(2'-cyanophenyl)phenylalanine, methyl ester (0.5 gm).

Step E (L)-4-(2'-Cyanophenyl)phenylalanine, methyl ester hydrochloride

Acetyl chloride (2 mL) was slowly added to a suspension of N-BOC-(L)-4-(2'-cyanophenyl)phenylalanine, methyl ester (0.5 gm, 1.3 mmol) in methanol (10 mL). The solution was stirred overnight at room temperature. The solvent was removed by rotoevaporation to yield (L)-4-(2'-cyanophenyl)phenylalanine, methyl ester hydrochloride (0.75 gm).

REFERENCE EXAMPLE 2

(L)-4-(2'-Cyanophenyl)phenylalanine, tert-butyl ester hydrochloride

Step A

N-BOC-(L)-4-Iodophenylalanine, tert-butyl ester

To a suspension of N-BOC-(L)-4-iodophenylalanine (BACHEM, 5.0 gm, 12.8 mmol) in methylene chloride (35 mL) and cyclohexane (70 mL) was added tert-butyl-2,2,2-trichloroacetimidate (2.93 gm, 13.4 mmol) followed by boron trifluoride (0.24 mL). The suspension was stirred at room temperature for 2 hr after which starting material still remained. Additional tert-butyl-2,2,2-trichloroacetimidate (2.93 gm, 13.4 mmol) and boron trifluoride (0.24 mL) were added and the reaction stirred at room temperature for four days. A third addition of tert-butyl-2,2,2-trichloroacetimidate (2.93 gm, 13.4 mmol) and boron trifluoride (0.24 mL) were added and the reaction stirred at room temperature for 3 hr. The mixture was filtered through a Celite filter pad which was subsequently washed with fresh methylene chloride:cyclohexane (1:1, 2×25 mL). The solvent was removed by rotoevaporation and the residue purified by flash column chromatography on silica gel eluted with 10% ether in hexane to yield N-BOC-(L)-4-iodophenylalanine, tert-butyl ester as a white crystalline solide (3.3 gm).

Step B (L)-4-(2'-Cyanophenyl)phenylalanine, tert-butyl ester hydrochloride

N-BOC-(L)-4-Iodophenylalanine, tert-butyl ester was converted to the title compound by the procedures described in Reference Example 1, Steps C through E.

REFERENCE EXAMPLE 3

(L)-4-(2'-methoxyphenyl)phenylalanine, tert-butyl ester

Step A
N-(BOC)-(L)-4-(2'-Methoxyphenyl)phenylalanine, tert-butyl ester

N-BOC-(L)-4-iodophenylalanine, tert-butyl ester (7.97 g (0.018 mol) was dissolved in 2:1 toluene:ethanol (160 mL). To this solution was added 2-methoxyphenylboronic acid (2.99 g, 20 mmol), tetrakistriphenylphosphine palladium(0) (0.69 g, 0.60 mmol) and a 2.0 M aqueous solution of sodium carbonate (22.7 mL, 0.45 mol). The reaction mixture was degassed three times and then heated at 90° C. for 90 minutes at which time the reaction mixture turned black. The mixture was diluted with ethyl acetate (300 mL) and was washed with water (3×150 mL) and brine (2×100 mL) and was dried over anhydrous MgSO$_4$. The mixture was filtered and concentrated in vacuo. The residue was purified by flash column chromatography on silica gel eluted with 10% EtOAc in hexanes to give 6.89 g (88% yield) of N-(BOC)-(L)-4-(2'-methoxyphenyl)phenylalanine, tert-butyl ester as a white solid.

300 MHz $^1$H NMR (CDCl$_3$): δ1.45 (s, 18H); 3.10 (d, 2H); 3.80 (s, 3H); 4.5 (dd, 2H); 5.1 bd, 1H); 7.0 (m, 2H); 7.22 (d, 2H); 7.30 (d, 2H); 7.49 (d, 2H); 7.62 (d, 2H).

Step B
(L)-4-(2'-Methoxyphenyl)phenylalanine, tert-butyl ester hydrochloride

N-(BOC)-(L)-4-(2'-Methoxyphenyl)phenylalanine, tert-butyl ester (8.64 g, 20 mmol) was dissolved in tert-butyl acetate (150 mL) to which was added of concentrated sulfuric acid (9.8 g, 100 mmol). The reaction mixture was stirred for 3 hours at room temperature and then diluted with ethyl acetate (150 mL). Addition of 1N NaOH was continued until the solution was basic. The aqueous phase was extracted with EtOAc (4×100 mL) and the combined organic phases were dried over anhydrous MgSO$_4$, filtered and concentrated in vacuo. The residue was dissolved in 100 mL of ether and treated with anhydrous HCl gas with cooling to give a white solid. The solid was recovered by filtration to give 5.8 g of (L)-4-(2'-methoxyphenyl)phenylalanine, tert-butyl ester hydrochloride. 400 MHz $^1$H-NMR (CD$_3$OD): 1.42 (s, 9H); 3.20 (d, 2H); 3.79 (s, 3H); 4.20 (t, 1H); 7.00 (t, 1H); 7.06 (d, 1H); 7.25 (dd, 1H); 7.32 (m, 3H); 7.50 (d, 2H).

REFERENCE EXAMPLE 4

(L)-4-(2',6'-(Dimethoxyphenyl)-phenylalanine, tert-butyl ester hydrochloride

Step A
N-(BOC)-4-[(Trifluoromethylsulfonyl)oxy]-(L)-phenylalanine, tert-butyl ester To a solution of of N-(BOC)-(L)-tyrosine, tert-butyl ester (18.5 g, 55 mmol) in 150 mL of dry methylene chloride was added pyridine (17.4 g, 220 mmol) followed at 0° C. by the dropwise addition of of neat triflic anhydride (18.6 g, 66 mmol). The reaction mixture was stirred at 0° C. and monitored by TLC. After 4 hours, the mixture was diluted with 200 mL of methylene chloride and was washed successively with 1N HCl (3×100 mL), saturated sodium bicarbonate (2×100 mL) and brine (1×50 mL). The solution was dried over anhydrous MgSO4, filtered and concentrated in vacuo to give N-(BOC)-4-[(trifluoromethylsulfonyl)oxy]-(L)-phenylalanine, tert-butyl ester as an oil which was used without further purification.

Step B
N-(BOC)-(L)-4-(2',6'-(Dimethoxyphenyl)-phenylalanine, tert-butyl ester, hydrochloride N-(BOC)-4-[(trifluoromethylsulfonyl)oxy]-(L)-phenylalanine, tert-butyl ester (Step A) was dissolved in a mixture of 125 mL of toluene and 61 mL of ethanol. To this solution was added 2,6-dimethoxyboronic acid (11.3 g, 62 mmol) and palladium tetrakistriphenylphosphine (2.5 g). The solution was treated with of potassium carbonate (18.3 g, 133 mmol) dissolved in 30 mL of water. The mixture was heated to reflux over 4 hours, cooled to room temperature, and then diluted with 200 mL of ethyl acetate. The solution was washed with water (3×75 mL) and brine (1×75 mL) and was dried over anhydrous MgSO$_4$. The mixture was filtered and concentrated in vacuo and the residue was purified by flash column chromatography on silica gel eluted with a gradient of 5–20% EtOAc in hexanes to provide 14.7 g of N-(BOC)-(L)-4-(2',6'-(dimethoxyphenyl)-phenylalanine, tert-butyl ester, hydrochloride as a white solid.

Step C
(L)-4-(2',6'-(Dimethoxyphenyl)-phenylalanine, tert-butyl ester hydrochloride N-(BOC)-(L)-4-(2',6'-(Dimethoxyphenyl)-phenylalanine, tert-butyl ester, hydrochloride (Step B) was dissolved in 350 mL of tert-butyl acetate at 0° C. and was treated with 8.3 mL of concentrated sulfuric acid. The cold bath was removed and after one hour TLC indicated only starting material was present. The reaction mixture was cooled in an ice bath once more and treated with 3.4 mL of concentrated sulfuric acid. The reaction was monitored by TLC. After consumption of the starting material the reaction mixture was diluted with 300 mL of ethyl acetate and was washed with 3×100 mL of 1N NaOH followed by brine (1×100 mL). The solution was dried over anhydrous MgSO4. Filtered and was concentrated in vacuo to provide 8.9 g of (L)-4-(2',6'-(dimethoxyphenyl)-phenylalanine, tert-butyl ester hydrochloride. 500 MHz $^1$H NMR (CD$_3$OD): δ1.45 (s, 9H), 3.20 (d, 2H); 3.69 (s, 6H); 4.20 (t, 1H); 6.72 (d, 2H), 7.15 (m, 5H).

REFERENCE EXAMPLE 5

3(R)-Amino-3-(4-biphenyl)propionic acid, methyl ester

Step A
N-(BOC)-(S)-4-Hydroxyphenylglycine

To a solution of (S)-(4-hydroxyphenyl)glycine (Sigma Chemical, 6.5 g, 39 mmol) in dioxane/water (1:1, 120 mL) was added triethylamine (5.9 g, 8.2 mL, 58 mmol) and [2-(tert-butoxycarbonyloxyimino)-2-phenylacetonitrile] (BOC-ON; 11 g, 45 mmol). After stirring overnight at room temperature, 300 mL of brine was added to the solution and the mixture was extracted with ether. (3×100 mL). The aqueous layer was acidified with HCl (pH=2) and extracted with 3×100 mL of ethyl acetate. The ethyl acetate layer was dried over anhydrous MgSO$_4$, filtered and the solvent removed under reduced pressure. The residue was purified by flash column chromatography eluted with a gradient of 2–5% methanol in methylene chloride to yiled 12 g of crude N-(BOC)-(S)-4-hydroxyphenylglycine. An impurity was removed following esterification of the product in the next step.

400 MHz $^1$H NMR (CDCl$_3$): δ1.37 (s, 9H), 5.1 (1H, br s), 6.7 (d, 2H, J=8 Hz), 7.15 (d, 2H, J=8 Hz).

Step B
N-(BOC)-(S)-4-hydroxyphenylglycine, methyl ester

In a 50 mL round bottomed flask was added a 1:1 mixture of benzene:methanol and N-(BOC)-(S)-4-hydroxyphenylglycine (2.8 g, 11 mmol). The solution was cooled to 0° C. and a 2 M solution of trimethylsilyldiazomethane (Aldrich Chemical Co.) in hexane was added with vigorous stirring until a slight yellow color persisted. The solvents were removed under reduced pressure and the crude product was purified by flash column chromatography (20% EtOAc in hexanes) to give N-(BOC)-(S)-4-hydroxyphenylglycine, methyl ester (2.05 g, 7.3 mmol) (66% yield).

300 MHz $^1$H NMR (CDCl$_3$): $\delta$1.43 (s, 9H), 3.71 (s, 3H), 5.22 (br d, 1H), 5.57 (1H, br d), 5.80 (br s, 1H), (6.7 (d, 2H, J=8 Hz), 7.17 (d, 2H, J=8 Hz).

Step C
N-(BOC)-(S)-4-[(Trifluoromethylsulfonyl)oxy] phenylglycine, methyl ester

To a 25 mL round bottom flask fitted with a stir bar and septum was added N-(BOC)-(S)-4-hydroxyphenylglycine, methyl ester (1.9 g, 6.8 mmol) and pyridine (2.8 mL, 33 mmol) in 12 mL methylene chloride. The flask was purged with N$_2$, cooled to 0° C. and trifluoromethanesulfonic anhydride (1.38 mL, 7.8 mmol) was added dropwise over several minutes, keeping the temperature at or below 4° C. The solution was stirred for 1 h, then at room temperature for 4 h. The mixture was diluted with 20 mL of methylene chloride. The mixture was washed with 20 mL of 0.5 N NaOH, 1×20 mL of water and 2×20 mL of 10% citric acid. The organic layer was dried over anhydrous MgSO4, filtered, and the solvents removed by evaporation in vacuuo. The residue was purified by flash column chromatography on silica gel eluted with 25% methylene chloride in hexane and gave 2.3g of N-(BOC)-(S)-4-[(trifluoromethylsulfonyl)oxy]phenylglycine, methyl ester. (81% yield).

300 MHz $^1$H NMR (CDCl$_3$): $\delta$1.43 (s, 9H), 3.74 (s, 3H), 5.35 (1H, br d), 5.68 (br s, 1H), 7.27 (d, 2H, J=8 Hz), 7.47 (d, 2H, J=8 Hz).

Step D
N-(BOC)-(S)-(4-Biphenyl)glycine

To a 25 mL round bottom flask fitted with a stir bar and septum was added N-(BOC)-(S)-4-trifluoromethylsulfonyloxyphenylglycine, methyl ester (690 mg, 1.67 mmol), anhydrous potassium carbonate (348 mg, 2.6 mmol) and benzeneboronic acid (411 mg, 3.4 mmol) in 15 mL of toluene and 3 mL of ethanol. The mixture was degassed under nitrogen with three freeze-thaw cycles and tetrakis(triphenylphosphine) palladium (94 mg, 0.085 mmol) was added to the reaction mixture and the mixture was heated between 75–90° C. for 4 h. The solvent was removed under reduced pressure and the residue purified by flash column chromatography on silica gel eluted with 15% EtOAc in hexane to give 600 mg of N-(BOC)-(S)-(4-biphenyl)glycine, methyl ester. 300 MHz 1H NMR (CDCl$_3$): $\delta$1.44 (s, 9H), 3.75 (s, 3H), 5.37 (1H, br d), 5.62 (br s, 1H), 7.36 (m,.1H), 7.45 (m, 4H), 7.57 (m, 4H).

The ester was hydrolyzed with 1.2 eq of KOH in 10 mL of 4:1 ethanol: water (2 h). The solution was acidified with 2 N HCl (pH=2). Solvent was removed in vacuo and the free acid was extracted with methylene chloride to provide 430 mg of N-(BOC)-(S)-(4-biphenyl)glycine (66% yield).

Step E
3-(BOC)amino-1-diazo-3-(4-biphenyl)propan-2-one

To a 25 mL round bottom flask fitted with a stir bar and septum was added N-(BOC)-(S)-4-biphenylglycine (430 mg, 1.31 mmol) in 10 mL of 2:1 methylene chloride: ether. The mixture was cooled to 0° C. and N-methylmorpholine (159 µl, 1.44 mmol) was added, followed by dropwise addition of isobutylchloroformate (179 µL, 1.38 mmol). The mixture was stirred for 1 h at 0° C., then diazomethane in ether (excess, prepared from Diazald® by literature procedure) was added dropwise to the reaction mixture. The mixture was stirred for 1 hr then quenched with saturated sodium bicarbonate. The mixture was extracted with ethyl acetate. (2×5 mL), washed with brine then dried over anhydrous MgSO4. The mixture was filtered, the solvent removed under reduced pressure and the product isolated by flash column hromatography on silica gel eluted with 15% EtOAc in hexane to give 280 mg (0.78 mmol) of 3-(BOC) amino-1-diazo-3-(4-biphenyl)propan-2-one (58% yield).

300 MHz $^1$H NMR (CDCl$_3$): $\delta$1.42 (s, 9H), 5.22 (bs, 1H), 5.29 (s, 1H), 5.9 (br s, 1H), 7.35–7.5 (m, 5H), 7.52–7.62 (m, 4H).

Step F
3(R)-Amino-3-(4-biphenyl)propionic acid, methyl ester

To a 25 mL round bottom flask fitted with a stir bar and septum was added 3-(BOC)amino-1-diazo-3-(4-biphenyl) propan-2-one (280 mg, 0.76 mmol), with 5 mL each of methanol and dioxane. The flask was cooled to 0° C. and 0.15 eq (34 mg, 0.038 mmol) of silver benzoate in 500 µl of triethylamine was added dropwise to the reaction mixture and the mixture allowed to stir at 25° C. for 1 h. The reaction was treated with 10% NH$_4$OH in saturated NH$_4$Cl (10 mL), then extracted with ether (3×10 mL), and the organic layer dried over anahydrous MgSO$_4$. After removal of solvents by evaporation in vacuo, the reside was purified by flash column chromatography on silica gel, eluted with 15% EtOAc in hexane. The 260 mg of product (98% yield) was dissolved in 10 mL of 1 N HCl in ethyl acetate. After stirring for 2 h at room temperature, 180 mg of 3(R)-amino-(4-biphenyl)propionic acid, methyl ester hydrochloride, was obtained by filitration.

300 MHz $^1$H NMR (CD$_3$OD): $\delta$2.90 (dd, 1H, J=18 Hz, J=6 Hz), 3.02 (dd, 1H, J=18 Hz, J=6 Hz), 3.66 (s, 3H), 5.9 (br s, 1H), 7.33–7.5 (m, 5H), 7.55–7.6 (m, 4H).

The following 3(R)-amino-propionic acid derivatives were prepared by the procedures described in Example 5 substituting the appropriate arylboronic acid analog for benzeneboronic acid:

REFERENCE EXAMPLE 6

3(R)-amino-3-(4-(2'-methoxyphenyl)phenyl) propionic acid, methyl ester

REFERENCE EXAMPLE 7

3(R)-amino-3-(4-(2',6'-dimethoxyphenyl)phenyl) propionic acid, methyl ester

REFERENCE EXAMPLE 8

(L)-4-((2',6'-dichloro)benzamido)-phenylalanine, methyl ester hydrochloride

Step A
N-(BOC)-(L)-4-((2',6'-dichloro)benzamido)-phenylalanine, methyl ester

N$_{(\alpha)}$-(BOC)-(L)-4-(FMOC-amino)-phenylalanine, methyl ester (9.62 g, 18.6 mmol) was dissolved in 15 mL of DMF and treated with diethylamine(11.6 mL, 112 mmol). The reaction mixture was stirred at room temperature for two hours, then concentrated in vacuo to give an viscous oil. This residue was dissolved in CH$_2$Cl$_2$ (50 mL ) then treated with diisopropylethylamine (5.16 mL, 27.9 mmol) and 2,6-dichlorobenzoyl chloride (2.93 mL, 20.4 mmol). The reaction mixture was stirred overnight at room temperature and then quenched with H$_2$O (40 mL). The layers were separated and the aqueous layer was extracted with CH$_2$Cl$_2$ (2×40 mL). The combined organic layers were combined and washed with brine (1×200 mL) then dried over anhydrous MgSO4. The mixture was filtered and concentrated in vacuo, then the residue was purified by flash column chromatography eluted with 50% EtOAc in hexane to give N-(BOC)-(L)-4-((2',6'-dichloro)benzamido)-phenylalanine, methyl ester (7.3 g).

500 MHz $^1$H NMR (CDCl$_3$): 1.44 (s, 9H); 3.12 (m, 2H); 3.75 (s, 3H); 4.61 (m, 1H); 5.00 (d, 1H); 7.15 (d, 2H); 7.32 (m, 3H); 7.59 (d, 2H).

Step B
(L)-4-((2',6'-dichloro)benzamido)-phenylalanine, methyl ester hydrochloride N-(BOC)-(L)-4-((2',6'-dichloro)benzamido)-phenylalanine, methyl ester (2.50 g, 5.35 mmol) was dissolved in dioxane (5 mL) and treated with HCl in EtOAc (18.4 mL of 2.9 N). The mixture was stirred overnight at room temperature, then concentrated in vacuo to give a quantitative yield of (L)-4-((2',6'-dichloro)benzamido)-phenylalanine, methyl ester hydrochloride.

500 MHz $^1$H NMR (CD$_3$OD): 3.17 (m, 1H); 3.28 (m, 1H); 3.84 (s, 3H); 4.33 (m, 1H); 7.28 (d, 2H); 7.46 (m, 3H); 7.68 (d, 2H).

The following examples are provided to more fully illustrate the invention and are not to be construed as limiting the invention in any manner.

EXAMPLE 1

N-(2-(3,4,5,6-tetrahydropyridy))-(L)-4-(2',6'-dimethoxyphenyl)phenylalanine, trifluoroacetic acid salt

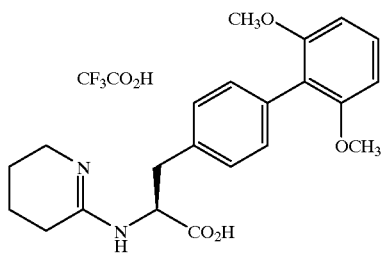

Step A
N-(2-(3,4,5,6-Tetrahydropyridyl))-(L)-4-(2'6'-dimethoxyphenyl)phenylalanine, tert-butyl ester (L)-4-(2',6'-(dimethoxyphenyl)-phenylalanine, tert-butyl ester hydrochloride (0.010 g, 0.035 mmol) from Reference Example 4 was dissolved in ethanol (0.2 mL) and treated with 2-methylthio-3,4,5,6-tetrahydropyridine hydriodide (0.0098 g, 0.039 mmol) and triethylamine (0.010 ml, 0.072 mmol). The mixture was stirred at room temperature for 4 hr then concentrated in vacuo. The reside was purified by flash column chromatography on silica gel eluted with 5% methanol containing 4% ammonium hydroxide in methylene chloride to give N-(2-(3,4,5,6-tetrahydropyridyl))-(L)-4-(2'6'-dimethoxyphenyl)phenylalanine, tert-butyl ester (12 mg). mass spectrum m/e=439.24 (M$^+$).

Step B
N-(2-(3,4,5,6-tetrahydropyridyl))-(L)-4-(2',6'-dimethoxyphenyl)phenylalanine, trifluoroacetic acid salt N-(2-(3,4,5,6-tetrahydropyridyl))-(L)-4-(2'6'-dimethoxyphenyl)-phenylalanine, tert-butyl ester (12 mg) was dissolved in 0.2 mL of methylene chloride and treated with 0.2 mL of trifluoroacetic acid at room temperature. After stirring for 18 hr, the resulting solution was concentrated in vacuo to give N-(2-(3,4,5,6-tetrahydropyridyl))-(L)-4-(2',6'-dimethoxyphenyl)phenylalanine, trifluoroacetic acid salt as a yellow solid (7 mg).

Mass spectrum: m/e=383.30 (M$^+$).

EXAMPLE 2

Inhibition of VLA-4 Dependent Adhesion to BSA-CS-1 Conjugate

Step A
Preparation of CS-1 Coated Plates

Untreated 96 well polystyrene flat bottom plates were coated with bovine serum albumin (BSA; 20 mg/ml) for 2 hours at room temperature and washed twice with phosphate buffered saline (PBS). The albumin coating was next derivatized with 10 mg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 mg/ml and allowed to react for 2 hours at room temperature. The plates were washed twice with PBS and stored at 4° C.

Step B
Preparation of Fluorescently Labeled Jurkat Cells

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 mg/ml streptomycin and 2 mM glutamine. Fluorescence activated cell sorter analysis with specific monoclonal antibodies confirmed that the cells expressed both the α4 and α1 chains of VLA-4. The cells were centrifuged at 400×g for five minutes and washed twice with PBS. The cells were incubated at a concentration of 2×10$^6$ cells/ml in PBS containing a 1 mM concentration of a fluorogenic esterase substrate (2',7'-bis-(2-carboxyethyl)-5-(and -6)-carboxyfluorescein, acetoxymethyl ester; BCECF-AM; Molecular Probes Inc., Eugene, Oreg.; catalog #B-1150) for 30–60 minutes at 37° C. in a 5% CO$_2$/air incubator. The fluorescently labeled Jurkat cells were washed two times in PBS and resuspended in RPMI containing 0.25% BSA at a final concentration of 2.0×10$^6$ cells/ml.

Step C
Assay Procedure

Compounds of this invention were prepared in DMSO at 100× the desired final assay concentration. Final concentrations were selected from a range between 0.001 nM-100 mM. Three mL of diluted compound, or vehicle alone, were premixed with 300 mL of cell suspension in 96-well polystyrene plates with round bottom wells. 100 mL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the IC$_{50}$ was determined from a ten point titration using a validated four parameter fit algorithm.

EXAMPLE 3

Antagonism of VLA-4 Dependent Binding to VCAM-Ig Fusion Protein

Step A
Preparation of VCAM-Ig

The signal peptide as well as domains 1 and 2 of human VCAM (GenBank Accession no. M30257) were amplified by PCR using the human VCAM cDNA (R & D Systems) as template and the following primer sequences: 3'-PCR primer: 5'-AATTATAATTTGATCAACTTAC CTGTCAATTCTTTTACAGCCTGCC-3';
5'-PCR primer:
5'-ATAGGAATTCCAGCTGCCACCATGCCTGGGAA GATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:
MPGKMVVILGASNILWIMFAASQAFKI-ETTPESRYLAQIGDSVSLTCSTTGCES
PFFSWRTQIDSPLNGKVTNEGTTSTLTM-NPVSFGNEHSYLCTATCESRKLEKGI
QVEIYSFPKDPEIHLSGPLEAGK-PITVKCSVADVYPFDRLEIDLLKGDHLMKSQ
EFLEDADRKSLETKSLEVTFT-PVIEDIGKVLVCRAKLHIDEMDSVPTVRQAVK EL.
The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 mg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B
Preparation of $^{125}$I-VCAM-Ig

VCAM-Ig was labeled to a specific radioactivity greater that 1000 Ci/mmole with $^{125}$-Bolton Hunter reagent (New England Nuclear, Boston, Mass.; cat # NEX120-0142) according to the manufacturer's instructions.The labeled protein was separated from unincorporated isotope by means of a calibrated HPLC gel filtration column (G2000SW; 7.5×600 mm; Tosoh, Japan) using uv and radiometric detection.

Step C
VCAM-Ig Binding Assay

Compounds of this invention were prepared in DMSO at 100× the desired final assay concentration. Final concentrations were selected from a range between 0.001 nM-100 μM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM $MnCl_2$; (ii) 20 μL of I- VCAM-Ig in binding buffer containing 1 mM $MnCl_2$ (final assay concentration~100 pM); (iii) 2.5 μL of compound solution or DMSO; (iv) and 0.5×10$^6$ cells in a volume of 30 mL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Contol wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 4

Antagonism of $\alpha_4\beta_7$ Dependent Binding to VCAM-Ig Fusion Protein

Step A
$\alpha_4\beta_7$ Cell Line

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/ 100 μg streptomycin/2 mM L-glutamine at 37° C., 5% carbon dioxide. The cells were pelleted at 1000 rpm for 5 minutes and then washed twice and resuspended in binding buffer (25 mM Hepes, 150 mM NaCl , 0.1% BSA, 3 mM KCl, 2 mM Glucose, pH 7.4).

Step B
VCAM-Ig Binding Assay

Compounds of this invention were prepared in DMSO at 100× the desired final assay concentration. Final concentrations were selected from a range between 0.001 nM-100 μM. Compounds were assayed in Millipore MHVB multiscreen plates (Cat# MHVBN4550) by making the following sequential additions to duplicate wells: (i) 100 ml/well of binding buffer containing 1.5 mM $MnCl_2$; (ii) 10 ml/well $^{125}$I-VCAM-Ig in binding buffer (final assay concentration <500 pM); (iii) 1.5 ml/well test compound or DMSO alone; (iv) 38 ml/well RPMI-8866 cell suspension (1.25×10$^6$ cells/ well). The plates were incubated at room temperature for 45 minutes on a plate shaker at 200 rpm, filtered on a vacuum box, and washed on the same apparatus by the addition of 100 mL of binding buffer containing 1 mM $MnCl_2$. After insertion of the multiscreen plates into adapter plates (Packard, Meriden, Conn., cat# 6005178), 100 mL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{50}$ was determined from a ten point titration using a validated four parameter fit algorithm.

What is claimed is:

1.

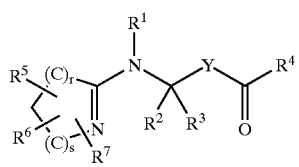

or a pharmaceutically acceptable salt thereof wherein: $R^1$ is
1) hydrogen,
2) $C_{1-10}$alkyl,
3) $C_{2-10}$alkenyl,
4) $C_{2-10}$alkynyl, wherein alkyl, alkenyl and alkynyl are optionally substituted with one to four substituents independently selected from $R^a$;

$R^2$ is
1) $C_{1-10}$alkyl,
2) $Ar^1$,
3) $Ar^1$—$C_{1-10}$alkyl,
4) $Ar^1$—$Ar^2$,
5) $Ar^1$—$Ar^2$—$C_{1-10}$alkyl-, wherein the alkyl group is optionally substituted with one to four substituents selected from $R^a$, and $Ar^1$ and $Ar^2$ are optionally substituted with one to four substituents independently selected from $R^b$;

$R^3$ is
1) hydrogen,
2) $C_{1-10}$alkyl,
3) $C_{2-10}$alkenyl,
4) $C_{2-10}$alkynyl, wherein alkyl, alkenyl and alkynyl are optionally substituted with one to four substituents independently selected from $R^a$;

$R^5$, $R^6$, and $R^7$ are independently selected from
1) hydroxy,
2) $C_{1-10}$alkoxy,
3) $C_{2-10}$alkenyl,
4) $C_{2-10}$alkynyl,
5) cycloalkyl,
6) heterocyclyl,
7) aryl;
8) aryl $C_{1-10}$alkyl,
9) heteroaryl;
10) heteroaryl $C_{1-10}$alkyl,
11) —$OR^d$,
12) —$NO_2$,
13) halogen
14) —$S(O)_mR^d$,
15) —$SR^d$,
16) —$S(O)_2OR^d$,
17) —$S(O)_mNR^dR^e$,
18) —$NR^dR^e$,
19) —$O(CR^fR^g)_nNR^dR^e$,
20) —$C(O)R^d$,
21) —$CO_2R^d$,
22) —$CO_2(CR^fR^g)_nCONR^dR^e$,
23) —$OC(O)R^d$,
24) —CN,
25) —$C(O)NR^dR^e$,
26) —$NR^dC(O)R^e$,
27) —$OC(O)NR^dR^e$,
28) —$NR^dC(O)OR^e$,
29) —$NR^dC(O)NR^dR^e$,
30) —$CR^d(N$—$OR^e)$,
31) —$CF_3$; or
32) —$OCF_3$;

wherein alkyl, alkenyl, alkynyl, cycloalkyl, heterocyclyl, aryl, heteroaryl are optionally substituted with one to four substituents selected from a group independently selected from $R^b$; or $R^5$ and $R^6$ together with the atom or atoms to which they are attached form a fused or spirocyclic ring of 4 to 7 members containing 0–2 heteroatoms independently selected from oxygen, sulfur and nitrogen;

$R^a$ is
1) hydrogen,
2) —$OR^d$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N$—$OR^3)$,
22) $CF_3$; or
23) —$OCF_3$;

$R^b$ is
1) a group selected from $R^a$,
2) $C_{1-10}$ alkyl,
3) $C_{2-10}$ alkenyl,
4) $C_{2-10}$ alkynyl,
5) cycloalkyl,
6) heterocyclyl,
7) aryl;
8) aryl $C_{1-10}$alkyl,
9) heteroaryl;
10) heteroaryl $C_{1-10}$ alkyl, wherein alkyl, alkenyl, alkynyl, cycloalkyl, heterocyclyl, aryl, heteroaryl are optionally substituted with one to four substituents selected from a group independently selected from $R^c$;

$R^c$ is
1) halogen,
2) —$NR^dR^e$,
3) carboxy,
4) cyano,
5) $C_{1-4}$alkyl,

6) $C_{1-4}$alkoxy,
7) aryl,
8) aryl $C_{1-4}$alkyl,
9) heteroaryl,
10) hydroxy,
11) —$CF_3$, wherein alkyl, alkenyl, alkynyl, cycloalkyl, heterocyclyl, aryl, heteroaryl are optionally substituted with one to four substituents selected from a group independently selected from $R^c$;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atoms to which they are attached form a heterocyclic ring of 4 to 7 members containing 0–2 additional heteroatoms independently selected from oxygen, sulfur and nitrogen;

$R^f$ and $R^g$ are independently selected from hydrogen, $C_{1-10}$alkyl, Cy and Cy—$C_{1-10}$alkyl; or $R^f$ and $R^g$ together with the carbon to which they are attached form a ring of 4 to 7 members containing 0–2 heteroatoms independently selected from oxygen, sulfur and nitrogen;

Cy is independently selected from cycloalkyl, heterocyclyl, aryl, or heteroaryl;

$Ar^1$ and $Ar^2$ are independently selected from aryl and heteroaryl;

m is an integer from 1 to 2;

n is an integer from 1 to 10;

r is an integer from 0 to 3;

s is an integer from 1 to 3;

r+s is an integer of 3;

Y is
1) a bond, or
2) —$CH_2$—.

2. A method for the prevention or treatment of diseases, disorders, conditions or symptoms mediated by cell adhesion in a mammal which comprises administering to said mamal a therapeutically effective amount of a compound of claim 1.

3. A method for the treatment of asthma, allergic rhinitis, multiple sclerosis, atherosclerosis, inflammatory bowel disease or inflammation in a mammal which comprises administering to said mammal a therapeutically effective amount of a compound of claim 1.

4. A pharmaceutical composition which comprises a compound of claim 1 and a pharmaceutically acceptable carrier thereof.

* * * * *

UNITED STATES PATENT AND TRADEMARK OFFICE
CERTIFICATE OF CORRECTION

PATENT NO. : 6,482,840 B2
DATED : November 19, 2002
INVENTOR(S) : William K. Hagmann, George A. Doherty and Shrenik Shah It is certified that error appears in the above-identified patent and that said Letters Patent is hereby corrected as shown below:

Column 31,
Lines 51 and 52, should read: -- 1) hydrogen,
2) $C_{1-10}$ alkyl, --.

Column 32,
Line 44, should read: -- 21) -$CR^d$(N-$OR^e$), --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,482,840 B2
DATED         : November 19, 2002
INVENTOR(S)   : William K. Hagmann et al.

It is certified that error appears in the above-identified patent and that said Letters Patent is hereby corrected as shown below:

Column 31,
Line 14, should read -- 1. A compound of the formula --
Lines 16 through 21, the structures should read

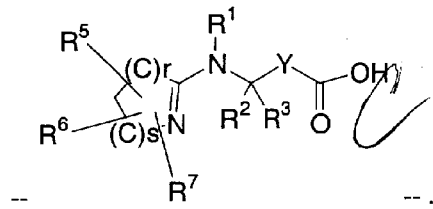

-- -- .

Signed and Sealed this

Twenty-fourth Day of June, 2003

JAMES E. ROGAN
*Director of the United States Patent and Trademark Office*